US005797950A

United States Patent [19]

Takashima

[11] Patent Number: 5,797,950

[45] Date of Patent: Aug. 25, 1998

[54] APPARATUS FOR RELEASING CONGESTED PROSTATE FLUID

[76] Inventor: Jiro Takashima, 7203 Schiller, Houston, Tex. 77055

[21] Appl. No.: 645,523

[22] Filed: May 14, 1996

[51] Int. Cl.$^6$ .......... A61M 29/00

[52] U.S. Cl. .......... 606/197; 128/67

[58] Field of Search .......... 606/191, 197–198; 128/61–62

[56] References Cited

U.S. PATENT DOCUMENTS

| | | | |
|---|---|---|---|
| 2,478,786 | 8/1949 | Smallen | 128/7 |
| 3,996,930 | 12/1976 | Sekulich | 128/67 |
| 4,002,164 | 1/1977 | Bradley | 128/62 |
| 4,542,753 | 9/1985 | Brenman et al. | 128/788 |
| 4,583,542 | 4/1986 | Boyd | 128/341 |
| 4,911,149 | 3/1990 | Borodulin et al. | 606/195 |
| 4,994,066 | 2/1991 | Voss | 606/191 X |
| 5,404,881 | 4/1995 | Cathaud et al. | 128/653 |

*Primary Examiner*—Michael Powell Buiz
*Assistant Examiner*—Nancy Mulcare
*Attorney, Agent, or Firm*—Harrison & Egbert

[57] ABSTRACT

An apparatus for releasing congested prostate fluid including a head having a size suitable for fitting in a human rectum and through a sphincter and having a surface suitable for rubbing a prostate gland, and a rod connected to a bottom of the head and extending outwardly therefrom. The rod serves to position the head and guide a movement of the head as the sphincter contracts and relaxes. An abutment surface is affixed to the rod distal the head. The abutment surface serves to contact a perineum area and to push up on the perineum area as the sphincter contracts. The rod is a rigid rod having a generally L-shaped or C-shaped configuration with a radius of curvature such that the head tilts toward the prostate gland as the sphincter contracts and draws the head upwardly. The head has a generally ellipsoidal shape. The head is formed of rubber-like material.

24 Claims, 3 Drawing Sheets

APPARATUS FOR RELEASING CONGESTED PROSTATE FLUID

TECHNICAL FIELD

The present invention relates to apparatus for the treatment of prostatitis. More particularly, the present invention relates to devices for massaging the prostate gland.

BACKGROUND ART

One treatment for non-bacterial disorder of prostate such as chronic prostatitis and a congested prostate is the prostate massage. Some urogolists believe that the most effective treatment for such prostatitis is for the doctor to massage the prostate at regular intervals. Other urogolists are far less enthusiastic about this procedure, and some do not believe in it at all. To perform such a massage, the physician simply inserts a gloved finger into the rectum and strokes the prostate very gently. It serves to relieve the symptoms of chronic prostatitis by draining accumulated prostatic fluid from the glands and ducts.

Given the difference of opinion of urogolists as to the need for prostatic massages, such massages can be difficult to obtain. In any event, the regular and repeated massaging of the prostate can often require frequent visits to the doctor's office. This causes the patient to incur a considerable expense and inconvenience. As such, a need has developed for allowing an individual to carry out his own prostatic massage.

In the past, some patents have issued relating to rectal devices. U.S. Pat. No. 4,542,753, issued on Sep. 24, 1985 to Brenman et al. describes an apparatus and method for stimulating penile erectile tissue. In this invention, a body is provided which may be inserted into the rectum of a user. The body is shaped so as to closely conform to the topological configuration of the rectum within the anal area to a site adjacent to the prostate gland. Electrical circuitry for generating a neurally stimulating electrical signal is located within the body. Electrodes, placed at particular locations on the surface of the body, apply the signal to the user. At least one of the electrodes closely contacts the prostate gland when the body member is operatively disposed, at a region or spot on the prostate gland previously determined to be sensitive to electrical stimulation.

U.S. Pat. No. 5,404,881, issued on Apr. 11, 1995, to Cathaud et al. describes a trans-rectal probe. This trans-rectal probe includes a probe body made of a flexible self-supporting polymer material whose degree of flexibility is designed to enable it to comply with the shape of the rectum while having substantially no compression effect on the rectum when inserted therein. The invention makes it possible to achieve accurate, safe and reliable positioning or an instrument for detection or therapeutic treatment level with the organ to be observed or treated. In particular, this device is designed for treatment of the prostate.

It is an object of the present invention to provide an apparatus which enables persons to carry out self-massages of the prostate so as to express the fluid from the congested prostate.

It is another object of the present invention to provide an apparatus which simultaneously provides finger pressure therapy on the perineum region.

It is a further object of the present invention to provide an apparatus for a prostate massage which is safe, easy to use, and relatively inexpensive.

These and other objects and advantages of the present invention will become apparent from a reading of the attached specification and appended claims.

SUMMARY OF THE INVENTION

The present invention is an apparatus for releasing congested prostate fluid that comprises a head means having a size suitable for fitting into a human rectum and through a sphincter and having a surface suitable for rubbing a prostate gland, and a rod means connected to a bottom of the head means and extending outwardly therefrom. The rod means serves to position the head and guide a movement of the head means as the sphincter contracts and relaxes. An abutment member is fixed to the rod means distal the head means so as to contact a perineum area and pushes the perineum area as the sphincter relaxes and contracts.

In the present invention, the rod means includes a rigid rod having a generally L-shaped configuration. The L-shaped configuration has a radius of curvature such that the head is positioned proximately to the prostate and tilts toward the prostate gland as the sphincter contracts and draws the head upwardly. The rod has a smaller diameter (approximately 1/8 inch) than a diameter of the head. The rod extends outwardly in a direction facing one side of the head. The head is tapered so as to narrow toward that one side. The rod is formed of a rigid material which has an adjustable angle of curvature.

The head is of a generally ellipsoidal shape having a diameter suitable for fitting into the human rectum. The head narrows in diameter toward the bottom of the head and adjacent to the rod. The head is formed of a rubber-like material. In particular, the head is covered with a lubricant-filled elastic material such that the head is movable within the elastic material. In the preferred embodiment of the present invention, the rod has a longitudinal axis which is coplanar with the longitudinal axis of the head.

The abutment surface includes a raised area which is affixed to an end of the rod opposite the head. This raised area extends upwardly from the rod so as to contact the perineum area when the head is in the rectum. The abutment surface is adjustably affixed to the rod so as to vary a distance from the head. The abutment surface also has an adjustable distance extending above the rod.

In an alternative embodiment of the present invention, the head has a configuration which conforms to the shape of an indented area on a front wall of the rectum above the sphincter. Also, in an alternative embodiment, a second rod branches from the first rod on an opposite side of the head.

DETAILED DESCRIPTION OF THE INVENTION

Figure 1:
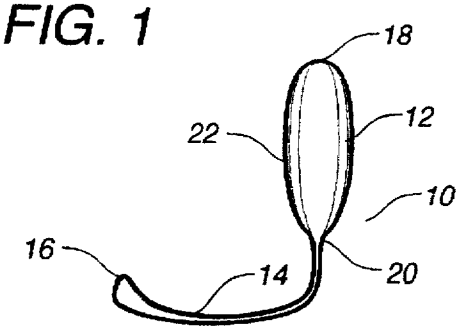
FIG. 1 is a side elevational view of the apparatus of the present invention.

FIG. 1 shows at 10 the apparatus of the present invention for releasing congested prostate fluid. The apparatus 10 includes a head 12, a rod 14 connected to a bottom of the head 12, and an abutment surface 16 in raised relationship relative to the rod 14.

In FIG. 1, it can be seen that the head 12 is an elongated member having a generally ellipsoidal configuration. In general, the head 12 tapers at the top 18 and also narrows in diameter toward the bottom 20 adjacent to the rod 14. The head 12 provides a surface 22 facing the abutment surface 16 to suitable for rubbing a prostate gland. The head 12 has a size suitable for fitting into a human rectum and through the sphincter.

Figure 3:
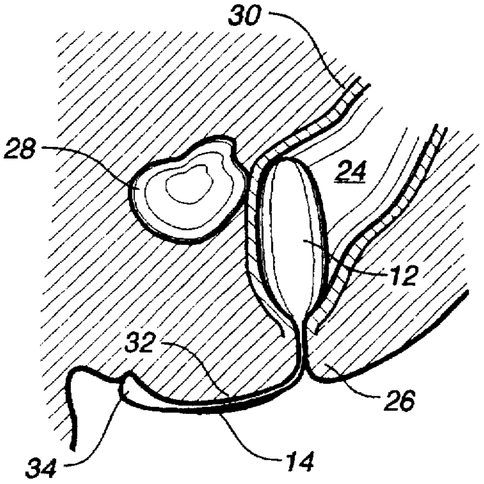
FIG. 3 is a cross-sectional view showing the operation of the apparatus of the present invention with the sphincter relaxed.
Figure 4:
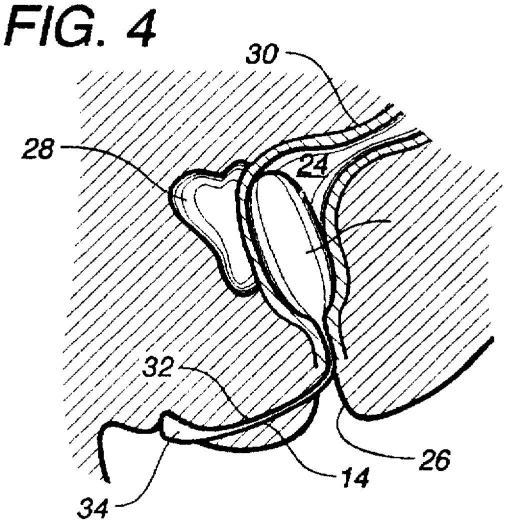
FIG. 4 shows the operation of the present invention with the sphincter contracted.

The rod 14 is connected to the bottom 20 of head 12. The rod 14 is a rigid and springy rod having a generally L-shaped configuration. This L-shaped configuration of the rod 14 has a radius of curvature such that the head 12 will tilt toward the prostate gland as the sphincter contracts and draws the head 12 upwardly (as shown in FIGS. 3 and 4). In particular, the rod 14 is configured so as to guide the movement of the head 12 as the sphincter contracts and relaxes. The rod 14 is made of high tension materials such as steel wire or plastics. The material for the rod 14 should be strong enough to hold the head 12 in position so as to adequately push and rub the prostate.

The abutment surface 16 extends upwardly from the rod 14 at an end of the rod 14 opposite the head 12. As can be seen, the abutment surface 16 gently curves upwardly so as to generally conform to the outer surface of the perineum area. The purpose of the abutment surface 16 is to contact and massage the perineum area as the head 12 of the apparatus moves upwardly and downwardly in the rectum. The abutment surface 16 also causes the head 12 to be positioned proximal the prostate. The abutment surface 16 serves to stimulate blood flow through finger pressure-like therapy. This massaging action is shown in FIG. 4.

Figure 2:
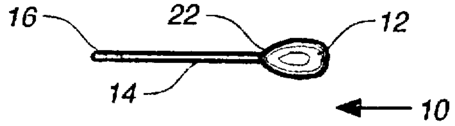
FIG. 2 is a plan view of the apparatus of FIG. 1.

FIG. 2 is a plan view of the apparatus 10. In particular, it can be seen that the head 12 has side 22 facing the rod 14 and the abutment surface 16. The head 12 narrows in diameter toward side 22. The narrow area of the side 22 creates greater forces that can be imparted onto the prostate. It can also be seen in FIG. 2 that the rod 14 and the abutment surface 16 are co-planar with the longitudinal axis of the head 12.

FIG. 3 shows the operation of the apparatus 10 of the present invention. In FIG. 3, it can be seen that the head 12 has been inserted into a rectum 24 through the sphincter 26. The head 12 is positioned by the rod in proximity to the prostate 28. The prostate 28 is rubbed through the wall 30 of the rectum 24. The head 12 is designed so as to reside in close proximity to the prostate 24 when the head 12 is inserted through the sphincter 26. The rod 14 extends outwardly through the sphincter 26 and wraps around onto the perineum area 32. The abutment surface 34 is configured so as to apply pressure to the perineum area 32 at the same time that the head 12 is massaging the prostate 28. As such, the apparatus 10 of the present invention massages the prostate 28 and also provides stimulation to the perineum area 34. FIG. 4 shows when the sphincter contracts, the head tilts to the prostate and the rod and the abutment thrust into the perineum area to give a good massage effect.

In operation, the apparatus 10 serves to treat prostatitis and to express fluid from the congested prostate gland. The angle of the rod 14 is formed so that the prostate area is rubbed by the pressure of the head 12. When the sphincter 26 contracts, the head 12 is pushed upwardly and tilts toward the prostate. The head 12 pushes the prostate 28 while the abutment surface 16 pushes up on the perineum region so as to squeeze the congested prostate fluid. It also serves to stimulate the perineum area 34 so as to improve blood circulation. The bottom portion of the head 12 is held by the upper edge of the sphincter and allows the head to move upwardly and downwardly within a defined range as the sphincter 26 contracts and relaxes. This gives a full massage effect onto the prostate 28. The head 12 moves to push the prostate 28 because the rod 14 is curved so as to cause the head 12 to tilt toward the prostate 28. As a result, the prostate is squeezed between the head and the rod. The rod, in combination with the head, serves as a stop, a positioner, and a squeezing mechanism. If it is necessary to alter the angle of the curve of the rod 14, the radius of curvature of the rod 14 can be easily reshaped so as to meet the requirements of the individual patient.

Figure 5:
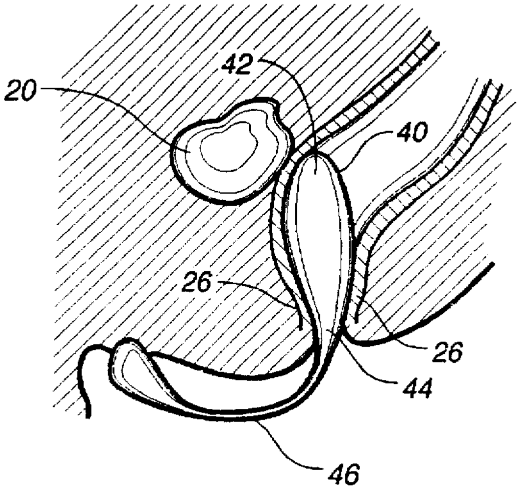
FIGS. 5 and 6 show the operation of an alternative embodiment of the present invention.
Figure 6:
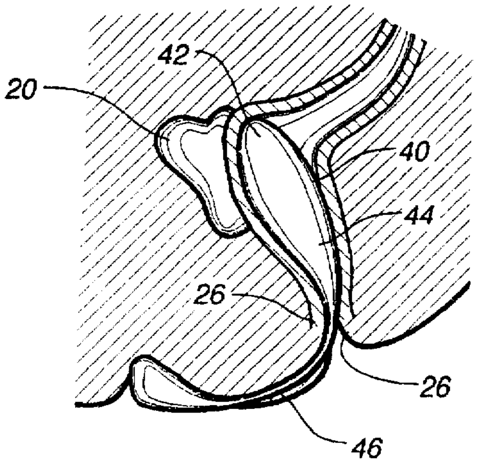

FIGS. 5 and 6 show an alternative embodiment 40 of the present invention. In the alternative embodiment 40, it can be seen that the head 42, although ellipsoidal in shape, has an area which conforms to the indented area on the front wall of the rectum 24 above the sphincter 26. The lower portion 44 of the head 42 is gently tapered toward the rod 46 for easier movement of the head 42 within the tile portion of the sphincter 26. The degree of curvature of the rod 46 is set so that when the sphincter 26 relaxes, the lower portion 44 of the head 42 is positioned at the tile area of the sphincter 26. As can be seen, the rod 46 has a generally C-shaped configuration. When the rod is C-shaped, the head 42 is guided along the curvature of the rod such that the head 42 pushes the prostate. In contrast, when the rod is L-shaped, the corner of the L-shaped rod thrusts into the sphincter so as to cause the head to draw upwardly and tilt toward the prostate. The massage effect to the perineum area is greater than with the C-shaped rod. When the sphincter contracts (as shown in FIG. 6), the sphincter pushes on the side of the lower portion 44 of the head 42 so as to push it upwardly. In the embodiment 40 of FIGS. 5 and 6, the length of the head movement is longer than that of the previous embodiment (shown in FIGS. 1–4). The length of head movement is approximately the total length between the tile portion of the sphincter 26 and the distance of the sphincter's movement.

In FIGS. 5 and 6, it can be seen how the shape of the inner face of the lower portion of the head 42 is gently curved so as to conform with the shape of the front indented portion of the rectum 24 above the sphincter 26. The rod 46 is continuously curved in a C-shaped configuration. When the sphincter 26 contracts, the head 42 is pulled up and guided by the angle of the curved rod 46. The abutment surface 50 at the end of the rod 46 opposite the head 42 deeply squeezes into the perineum area so as to further provide a "squeezing" effect. It can be seen that the inner surface of the head 42 strongly rubs against the prostate 28. The upper portion of the head 42 can be made of an elastically pliable material so as to conform with the front wall of the rectum 24 while giving suitable pressure onto the prostate 28. The rod 14 should be sufficiently thin so as to thrust through the elastic skin surface to give deeper and sharper stimulation on the perineum area and also providing more movement to the head 24 while maintaining a tight fit between the prostate 28 and the perineum region.

Figure 7:
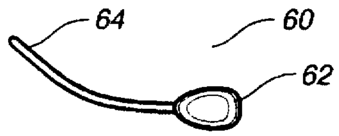
FIG. 7 is a plan view of the second alternative embodiment of the present invention.

In FIG. 7, an alternative embodiment 60 is illustrated by plan view. The alternative embodiment 60 includes a head 62 and a rod 64 extending from the head 62. Unlike the previous embodiment (in particular as shown in FIG. 2), the rod 64 is curved away from the lateral plane of the head 62. The apparatus 60 can be used in special cases in which the perineum region is particularly sensitive or in which contact should be avoided with the perineum region. In this embodiment, the rod 64 will contact a surface other than the perineum area.

Figure 8:
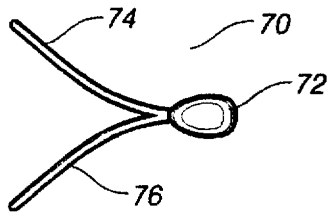
FIG. 8 is a plan view of a third alternative embodiment of the present invention.

In FIG. 8, an alternative embodiment 70 is illustrated in which a head 72 has rods 74 and 76 extending outwardly therefrom. The first rod 74 is curvedly offset from the lateral plane of the head 72 on one side of the lateral plane. The second rod 76 branches out of the first rod 74 and is curved on an opposite side of the lateral plane of the head 72. The embodiment of FIG. 7 is also used where the perineum region is particularly sensitive.

Figure 9:
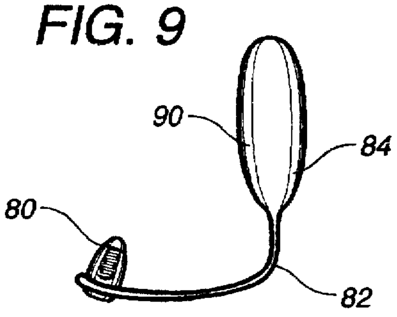
FIGS. 9 and 10 show the abutment surface as applied to the rod of the present invention.
Figure 10:
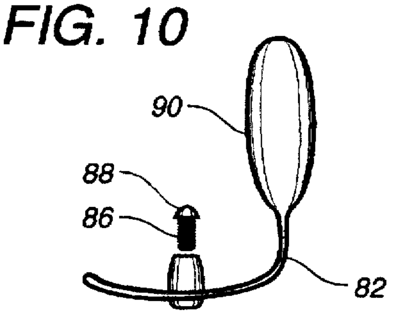

In FIGS. 9 and 10, it can be seen that an adjustable abutment surface 80 is affixed to the rod 82. Rod 82 is connected to a head 84. The abutment surface 80 is adjustable so as to be affixed along the length of the rod 82 a desired distance from the head 84. A threaded member 86 is provided on the abutment surface 80 so as to provide an elevated surface 88 a desired distance above the rod 82. In the embodiment of the present invention shown in FIGS. 8 and 9, the abutment surface 80 is suitably adjustable so as to fulfill the needs of the user. The height of the abutment surface is adjustable so as to change the angle with the inner face 90 of the head 84. The raised surface 88 can be elevated to further increase the "grabbing" power for the prostate area.

Figure 11:
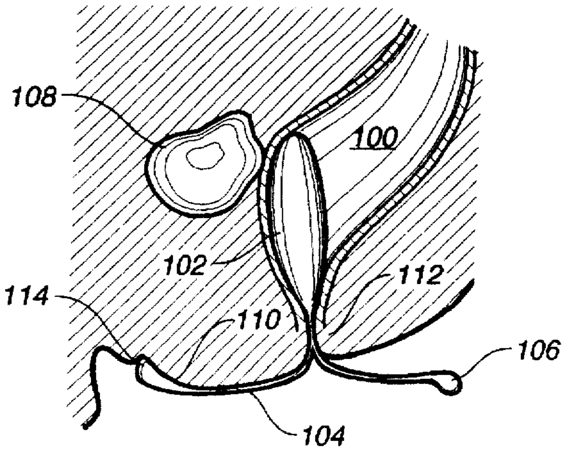
FIGS. 11 and 12 show the construction and use of a fourth alternative embodiment of the present invention.
Figure 12:
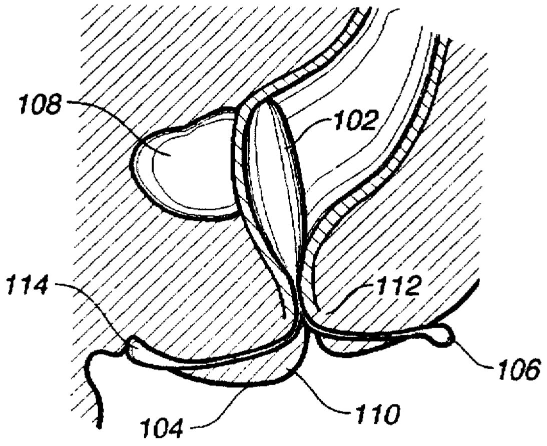

FIGS. 11 and 12 shows another alternative embodiment 100 of the present invention. The apparatus 100 includes a head 102 and a first rod 104 extending outwardly therefrom. A second rod 106 branches from the first rod 104 and extends in a direction opposite the first rod 104. The rod 106 serves as a push and a control rod for the head 102 and for the first rod 104. The rod 106 serves as a handle which can be pushed toward the body so that the prostate 108 and the perineum region 110 be squeezed between the head 102 and the rod 104 without the contraction of the sphincter 112. This can be carried out by a hands-free operation. The patient can lie on his back and rotate and rock the pelvis back and forth so as to find the most effective position for the massages. In addition, the sphincter 112 provides a contraction and relaxation motion so as to give the head 102 a linear massaging action on the prostate 108. Simultaneously, the rod 104 and its abutment surface 114 gives proper pressure to the perineum region.

The relationship of the first rod 104 and the second rod 106 are set so that when the sphincter 112 is contracting, the second rod 106 does not disturb the tilting of the head 102 toward the prostate 108. It also does not disturb the action of the head 102 upon the prostate 108 when the sphincter fully contracts. As a result, the head 102 is able to reach its furthest position so as to push on and rub the prostate 108. The second rod 106 can also serve as a stop for the excessive tilt of the head 102.

It is believed that the embodiment 100 provides for maximum treatment of the prostate 108. The second rod 106 serves as a push and a control rod. As shown in FIG. 12, when the second rod 106 is pushed all the way to the body, the prostate 108 and the perineum region 110 receive the maximum effect without contraction of the sphincter 112. In addition, the effect of the contraction and relaxation of the sphincter 112 serves to make the motion of the head 102 relatively stable with the pressure received from the second rod 106.

Figure 13:
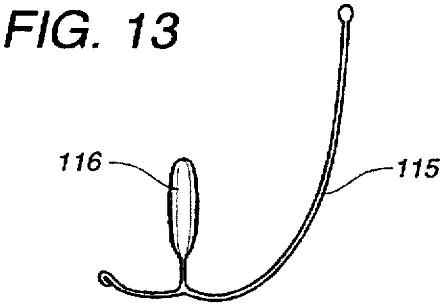
FIGS. 13–15 show a fifth alternative embodiment of the present invention, along with its operation and use.
Figure 14:
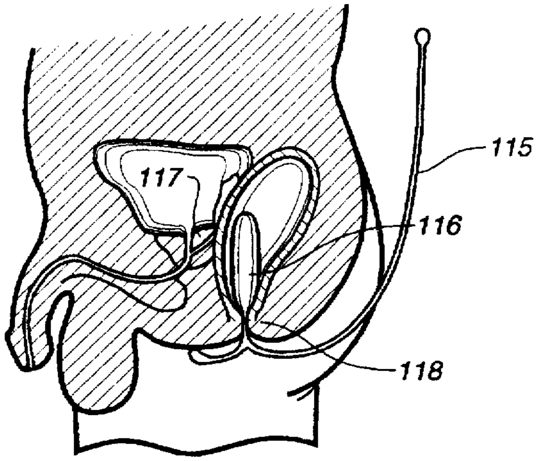
Figure 15:
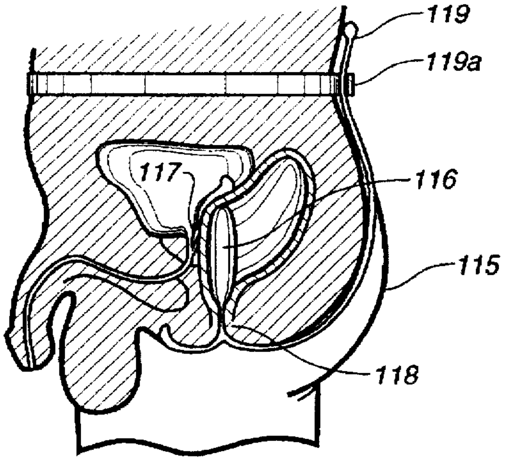

Referring to FIG. 13, the second rod 115 is extended and curved. The rod is made of a springy material, such as piano wire or high tension plastics. The angle of the curve is set so that when the handle 115 is pushed to the body (as shown in FIGS. 14 and 15), the outer face of the head 116 pushes the prostate 117. Since the handle 115 is made of springy materials, the angle of the curve has a wide range of tolerance in order to give relatively constant pressure to the prostate 117. Also, the thin rod (approximately ⅛") is easily moved laterally within the tile area of the sphincter 118. This helps the maneuverability of the head 116 to rub the prostate efficiently without intervention of the sphincter 118. The elastic limit of the rod 115 is chosen to limit, within a safety range, the movement of the head to push the prostate within a certain amount of the pressure, otherwise the rod 115 will yield to the stress.

FIG. 15 shows the end 119 of the rod 115 is pushed to the body by the rubber belt 119*a* of the pants so as to cause the head 116 to push the prostate 117.

Figure 16:
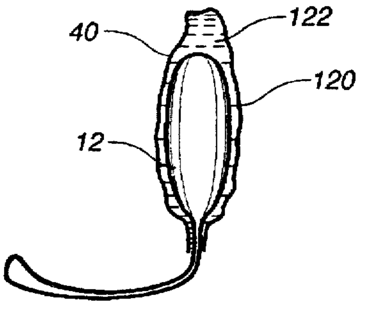
FIG. 16 is a cross-sectional view of head of the apparatus of the present invention.

In FIG. 16, it can be seen that the head 12 is covered with an elastic material 120 which is filled with a lubricant 122. The lubricant allows the head 12 to move inside the elastic material 120 so as to reduce friction between the head 12 and the wall of the rectum 24.

The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

I claim:

1. An apparatus for releasing congested prostate fluid comprising:

a head means having a size suitable for fitting into a human rectum and movably held by a sphincter, said head means having a surface for rubbing a prostate gland; and a rod means connected to a bottom of said head means and extending outwardly therefrom, said rod means for guiding a movement of said head means as the sphincter contracts and relaxes, said rod means comprising:

a rod having a generally L-shaped or C-shaped configuration, said rod having a first end proximal said head means and a second end distal said head means, said rod having a plane extending transversely therethrough at said first end which is separated by less than a length of the sphincter from a plane parallel thereto touching said second end.

2. The apparatus of claim 1, further comprising:

an abutment means affixed to said rod means distal said head means, said abutment means for contacting a perineum area as the sphincter contracts.

3. The apparatus of claim 2, said abutment means comprising:

a raised surface affixed to an end of said rod opposite said head.

4. The apparatus of claim 3, said surface being adjustably affixed to said rod so as to vary a distance of said abutment surface from said head.

5. The apparatus of claim 3, said abutment surface being adjustable so as to vary a distance above said rod.

6. The apparatus of claim 1.

said configuration of said rod having a radius of curvature such that said head is positioned close to the prostate and is guided toward the prostate gland as the sphincter contracts and draws said head upwardly in said rectum.

7. The apparatus of claim 6, said rod being formed of a rigid material having an adjustable angle of curvature.

8. The apparatus of claim 6, said head means having a longitudinal axis, said rod having a longitudinal axis coplanar with said longitudinal axis of said head.

9. The apparatus of claim 6, said head having a plane extending laterally therethrough, said rod having a longitudinal axis being curvedly offset from said plane extending laterally therethrough.

10. The apparatus of claim 9, said rod comprising:

a first rod extending outwardly from said head; and a second rod branching outwardly from said first rod.

11. The apparatus of claim 6, further comprising:

a second rod branching from said first rod on an opposite side of said head, said second rod having a curved configuration.

12. The apparatus of claim 11, said second rod branching from said first rod on an opposite side of said head, said second rod being a resilient wire having a U-shaped configuration.

13. In claim 12, said second rod having an elastic limit in which a safety range in which said head pushes the prostate within a certain amount of the pressure, and when the stress is greater than the elastic limit of the rod, the rod yields to the stress.

14. The apparatus of claim 1, said head means comprising:

a head having a generally ellipsoidal shape.

15. The apparatus of claim 14, said rod means having a smaller diameter than a diameter of said head, said rod means having a diameter of ⅛" or less.

16. The apparatus of claim 14, said rod means extending outwardly in a direction facing one side of said head means, said head being tapered so as to narrow toward said one side.

17. The apparatus of claim 14, said generally ellipsoidal configuration of said head conforming in shape to an indented area on a front wall of the rectum above the sphincter.

18. The apparatus of claim 14, said head narrowing in diameter toward said rod means at a bottom of said head.

19. The apparatus of claim 14, said head being formed of a firm rubberlike material.

20. The apparatus of claim 14, said head being covered with a lubricant-filled elastic material such that said head is movable within said elastic material.

21. The apparatus of claim 1, said rod having a C-shaped configuration, said second end of said rod for bearing against a perineum surface when said head means is held by the sphincter.

22. The apparatus of claim 21, said head means having a longitudinal axis extending therethrough, said second end having a surface for bearing against the perineum surface, said surface of said second end being on an imaginary line extending to said bottom of said head means, said imaginary line extending at an angle of less than 90 degrees relative to said longitudinal axis.

23. An apparatus for releasing congested prostate fluid comprising:

a head having a generally ellipsoidal shape with a diameter suitable for fitting into a human rectum and movably held by the sphincter; and a rod having one end connected to a bottom of said head and extending outwardly therefrom, said rod having a curved configuration, said rod having a first end proximal said head means and a second end distal said head, said rod having a plane extending transversely therethrough at said first end which is separated by less than ½ inch from a plane parallel thereto touching said second end.

24. The apparatus of claim 23, further comprising:

a raised abutment surface affixed to an end of said rod opposite said head.

* * * * *